US008285492B2

(12) United States Patent
Gunstream

(10) Patent No.: US 8,285,492 B2
(45) Date of Patent: Oct. 9, 2012

(54) SYSTEM AND METHOD FOR INTERPOLATIVE CALIBRATION

(75) Inventor: Stephen J. Gunstream, Redwood City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 12/534,742

(22) Filed: Aug. 3, 2009

(65) Prior Publication Data

US 2010/0198525 A1    Aug. 5, 2010

Related U.S. Application Data

(63) Continuation of application No. 12/022,094, filed on Jan. 29, 2008, now abandoned.

(60) Provisional application No. 60/898,064, filed on Jan. 29, 2007.

(51) Int. Cl.
*G01N 21/17* (2006.01)
*G01N 21/01* (2006.01)
*G01N 21/31* (2006.01)
*G01B 9/08* (2006.01)

(52) U.S. Cl. .................. 702/32; 702/30; 702/31; 702/40

(58) Field of Classification Search .................... 702/28, 702/85, 94, 131, 150, 170, 179, 182, 183; 204/452; 250/459.1; 422/82.08
See application file for complete search history.

(56) References Cited

U.S. PATENT DOCUMENTS

| | | | |
|---|---|---|---|
| 5,850,623 A * | 12/1998 | Carman et al. .................. 702/28 |
| 5,952,202 A | 9/1999 | Aoyagi et al. | |
| 6,387,621 B1 | 5/2002 | Wittwer | |
| 6,471,916 B1 | 10/2002 | Noblett | |
| 6,991,712 B2 * | 1/2006 | Sharaf et al. .................. 204/452 |
| 7,089,123 B2 | 8/2006 | Corson et al. | |
| 7,233,393 B2 | 6/2007 | Tomaney et al. | |
| 2002/0034745 A1 | 3/2002 | McMillan et al. | |
| 2006/0024690 A1 | 2/2006 | Kao et al. | |
| 2006/0102479 A1 * | 5/2006 | Sharaf et al. .................. 204/452 |
| 2006/0138344 A1 * | 6/2006 | Gunstream et al. ........ 250/459.1 |
| 2007/0248982 A1 | 10/2007 | Woo et al. | |
| 2008/0133198 A1 | 6/2008 | Carrick | |
| 2008/0154511 A1 | 6/2008 | Leong | |
| 2008/0154512 A1 | 6/2008 | Leong | |
| 2008/0178653 A1 | 7/2008 | Gunstream | |
| 2008/0182264 A1 | 7/2008 | Gunstream | |
| 2008/0209978 A1 | 9/2008 | Gunstream | |
| 2010/0198525 A1 | 8/2010 | Gunstream | |

OTHER PUBLICATIONS

U.S. Appl. No. 12/022,079, "Response to Jul. 15, 2010 Office action", filed Nov. 15, 2010, 12 pgs.

(Continued)

*Primary Examiner* — Mohamed Charioui
*Assistant Examiner* — Felix Suarez

(57) ABSTRACT

Systems and methods are provided for calibrating emission data or other information signals collected during a polymerase chain reaction (PCR), amplification reaction, assay, process, or other reaction. Calibration of multiple detectable materials can be achieved during a single cycle or run, or during a plurality of runs of the reaction. A reading from every well, container, or other support region of a sample support does not have to be taken. Interpolation can be used to determine values for emission data or other information signals that were not taken, or are unknown, using detected emission data, or other detected information signals. By calibrating the detected emission data and the interpolated data, a more accurate reading of emission data or information signal can be obtained.

18 Claims, 7 Drawing Sheets

OTHER PUBLICATIONS

U.S. Appl. No. 12/022,079, "Office action mailed Jul. 15, 2010", 7 pgs.
Roche Applied Science "Relative Quantification" Technical Note No. LC 13/2001, Published 2001. Retrieved from http://www.roche-applied-science.com, May 14, 2009.
U.S. Appl. No. 12/022,079 Office Action dated Nov. 17, 2009.
U.S. Appl. No. 12/022,079 Response to Nov. 17, 2009 Office Action filed May 14, 2010.
U.S. Appl. No. 12/022,087 Office Action dated Nov. 2, 2009.
U.S. Appl. No. 12/022,087 Response to Nov. 2, 2009 Office Action filed Apr. 30, 2010.
U.S. Appl. No. 12/022,087 Office Action dated Jun. 11, 2010.
U.S. Appl. No. 12/022,087 Response to Jun. 11, 2010 Office Action filed Nov. 12, 2010.
U.S. Appl. No. 12/022,087 Notice of Allowance dated Dec. 23, 2010.
U.S. Appl. No. 12/022,087 Notice of Allowance dated Apr. 18, 2011.
U.S. Appl. No. 12/022,094 Office Action dated Feb. 3, 2009.
U.S. Appl. No. 12/022,098 Office Action dated Mar. 16, 2009.

* cited by examiner

SYSTEM AND METHOD FOR INTERPOLATIVE CALIBRATION

RELATED APPLICATION

This application is a continuation of application Ser. No. 12/022,094 filed Jan. 29, 2008, which claims priority to Provisional Application No. 60/898,064, filed Jan. 29, 2007, both of which are incorporated herein by reference.

FIELD

The present application relates to biological testing devices, systems that contain such devices, and methods that use such devices and/or systems.

INTRODUCTION

In various known polymerase chain reaction (PCR) methods, better accuracy in the detection of an amplification signal, and hence original sample quantity, is frequently sought by calibrating each dye, fluorescent marker, or other reference material to be used in the PCR implementation. Such efforts reduce error in the emission signal coming from the sample container, for example, an amplification well. Such errors can result from the dye, the sample container, and other sources of background signal noise. Under current practice, calibration of such systems typically involves testing one dye at a time, and typically the entire well plate is filled with that one dye. Once the system has finished with that one dye, the plate must be removed and replaced, or cleaned, and a new dye inserted. The drawbacks of such a system include the expenditure of extensive amounts of time to calibrate for each of plurality of different dyes or other reference materials, a lack of uniformity between instruments, between well plates, and between dyes, and the inability to perform PCR, RT-PCR, or other assays, processes, or reactions while calibrating the emission signal. A need exists for a method of calibration and related techniques that addresses these and other issues.

SUMMARY

According to various embodiments, the present teachings relate to the calibration of PCR and real-time polymerase chain reaction ("RT-PCR") instruments. These methods, teachings, and systems, relate to calibrating or adjusting signals from a plurality of dyes over a single well plate, using less than all the wells, and then using interpolation to determine the unknown calibration signals for the wells which were skipped. By skipping wells and/or using multiple dyes at the same time, the calibration or adjustment process requires less time.

According to various embodiments, the present teachings also relate to methods for fixing a calibration, to algorithms for calibration, and to reference standards.

These and other features of the present teachings are set forth herein.

FIGURES

DESCRIPTION

Figure 1:
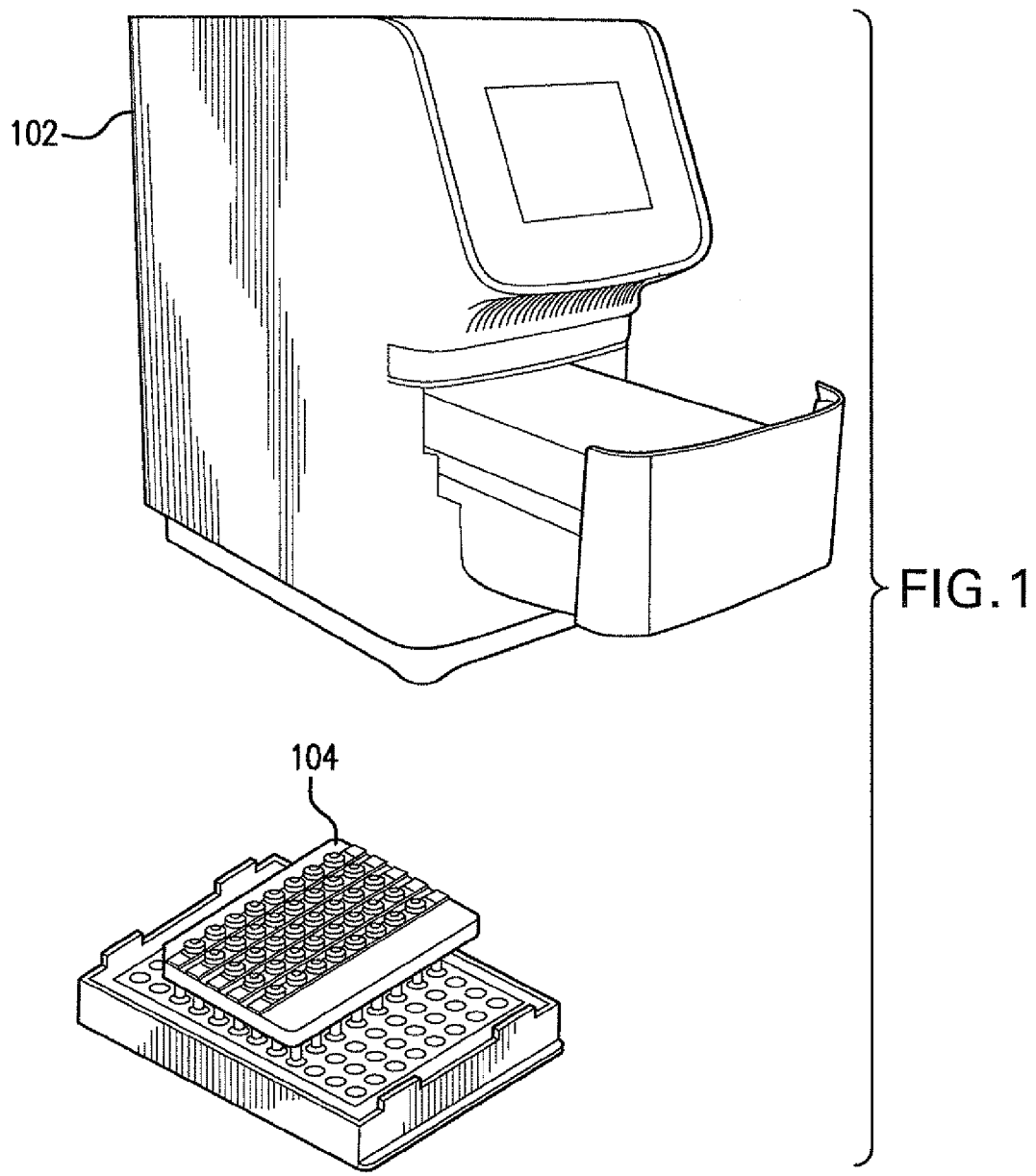
FIG. 1 illustrates an exemplary PCR machine and sample well plate, according to various embodiments.

According to various embodiments, a method of generating emission data for a sample support is provided. The method comprises providing a sample support comprising a plurality of support regions, loading a detectable material into the plurality of support regions such that at least one, but less than all, of the plurality of support regions contain the detectable material, receiving emission data values for the detectable material detected from at least two or more of the plurality of support regions, identifying at least one support region of the plurality of support regions, that did not emit an emission data value for the detectable material, and interpolating an emission data value for the at least one support region that did not emit an emission data value for the detectable material.

Herein, the term "emission" is used to exemplify a signal detected and/or calibrated according to various embodiments of the present teachings. It is to be understood that by "emission" the present teachings are referring to not only electromagnetic radiation but rather are also referring to any physical or chemical signal or other data that can be read, detected, imaged, or surmised from one or more area of interest, for example, a support region such as a well of a multi-well plate. "Emission" herein is intended to encompass electromagnetic radiation, optical signals, chemiluminescent signals, fluorescent signals, radiation transmission values, and radiation absorption values.

The method can further comprise calibrating the emission data with the received emission data, calibrating the emission data with the interpolated emission data, or calibrating the emission data with the received emission data and the interpolated emission data. The detectable material can comprise a dry material or a wet material. In some embodiments, the detectable material can comprise a dye, a fluorescent marker, or another reference material.

In some embodiments, the method can also comprise loading a second detectable material into the plurality of support regions such that at least one, but less than all, of the plurality of support regions contains the second detectable material, and identifying at least one support region of the plurality of support regions that did not emit an emission data value for at least one of the first and second detectable materials. In some embodiments, at least one of the first and second detectable materials can comprise a plurality of different detectable materials. Each of the first and second detectable materials can be equally distributed between two or more of the plurality of support regions. In some embodiments, at least one of the first and second detectable materials is distributed in the plurality of support regions according to a predetermined pattern of support regions of the sample support. The predetermined pattern can comprise an alternating pattern. In some embodiments, at least one of the first and second detectable materials is randomly distributed in the plurality of support regions. In some cases, one or more, for example, two or more of the plurality of support regions are left empty. According to various embodiments, support regions containing a first detectable material, support regions containing a second detectable material, and two or more empty support regions, are arranged according to a predetermined pattern on a sample support. The predetermined pattern can comprise an alternating pattern. In other embodiments, support regions containing a first detectable material, support regions containing a second detectable material, and two or more empty support regions, are randomly arranged.

In yet other embodiments, a method of interpolating signal information for a sample support is provided and comprises providing a sample support that comprises a plurality of support regions, loading a first detectable material into the plurality of support regions such that at least one, but less than all, of the plurality of support regions contains the first detectable material, loading at least a second detectable material into the plurality of support regions such that at least one, but less than all, of the plurality of support regions contains the second detectable material, receiving signal information values for at least one of the first and second detectable materials detected from two or more of the plurality of support regions, identifying at least one support region of the plurality of support regions, where signal information was not detected for at least one of the first and second detectable materials, and interpolating signal information for the at least one support region.

Various embodiments of the present teachings relate to systems and methods for spectral and other calibration of emission data detected from PCR, RT-PCR, or other instruments used to detect various reactions, amplifications, assays, processes, systems, and analyses. The calibration systems and methods can be implemented in or applied to scanning systems and methods, imaging systems and methods, biological scanning systems and methods, biological imaging systems and methods, assays, reactions, analyses, or other processes in which a read head containing a photodetector, photosensor, CCD device, CID device, or other optical detector, for example, a photodiode, can read fluorescent output, signal information, or other output from a sample well, container, or other support region. The detector can then travel to a location to read the spectral dye or other output at that location, and step or repeat across a plate, sample support, or other platform to take spectra from the entire group of sample wells, containers, or other support regions. The platform can comprise any type of well plate, sample support, or other platform capable of holding, containing, storing, or enclosing a material, for example, a microtiter or multiwell plate. The detector can be used to detect signals that are not optical, for example, a scanning electron microscope signal, a thermal signal, a radiation signal, or any other kind of signal.

According to some embodiments, the detector can take a reading from every well, container, or support region, throughout the well plate, sample support, or other platform, in which one, or more than one, dye, fluorescent marker, or reference material has been loaded. In some embodiments, the detector does not need to take a reading from every well, container, or support region of the well plate, sample support, or other platform. It will be appreciated that only a portion of the platform needs to be detected, for a calibration or an adjustment to be calculated, estimated, approximated, or otherwise determined. For example, only half of the wells, containers, or other support regions, can be filled with dye, fluorescent marker, or other reference material. The detector can take a reading for emission data from only those wells, containers, or support regions that have been filled or loaded with one or more dyes, fluorescent marker, or other reference material, herein also referred to as one or more detectable materials. In another example, all of the wells, containers, or support regions can be loaded with a dye, or multiple dyes, fluorescent marker, or other reference material and the detector can take a reading for emission data from only some of those wells, containers, or support regions, and skip across, or avoid some of the wells, containers, or other support regions. For those wells, containers, or other support regions that have been skipped, avoided, or left empty, an emission data value can be estimated, approximated, calculated, or otherwise determined using interpolation. It will be appreciated that different portions of the plate can be loaded, left empty, detected, skipped, and/or avoided.

The present teachings are intended to encompass the calibration of not only wells of a multiwell plate, but of locations on other platforms as well, for example, locations on gene chips, locations on hybridization arrays, and locations in flow cells. Such other platforms are also referred to herein as sample supports and such locations are also referred to herein as support regions.

According to various embodiments, the calibration systems and methods can be implemented in or applied to PCR imaging systems, or other instruments, systems, or apparatuses, in which a detector, for example, a scanning detector, an imaging detector, a CCD, a CID, a photodiode, a photodetector, or another detector, can image a portion of the entirety of a well plate, sample support, or other platform. An image or other detected signal can be taken from a portion of or from all of the sample wells, containers, or other support regions contained therein, all at one time or substantially all at one time. For example, the detector can take a spectral image of all 96 wells, or a portion of the 96 wells, of a standard microtiter plate. In some embodiments, the wells can be imaged one-at-a-time using a scanning technique, while in some embodiments more than one well can be imaged simultaneously, for example, using a CCD camera. Various types of instruments, systems, apparatuses, or other devices can be used, for example, as illustrated in FIG. 1, a PCR instrument 102 that is capable of holding a well plate 104.

According to various embodiments, each sample well, container, or other support region in a well plate, sample support, or other platform, can contain samples, for example, samples of DNA fragments or other materials. These samples can be affixed with one or more spectrally distinct dye, fluorescent marker, or other reference material, for detection and/or analysis. A calibration or adjustment can be performed to normalize, compensate, correct, adjust, or otherwise increase the consistency or accuracy of readings that have been taken from the sample wells, containers, or other support regions. The calibration or adjustment can correct or compensate for variations due to or affected by factors including, but not limited to, differences in signal strength, dye or sample concentrations, contaminations, spectral or amplitude distortions, deviations in optical paths, plate geometry, fluorescent noise floor, sample population or size, or other variations or anomalies that can arise from dye to dye, well to well, plate to plate, or instrument to instrument, among other corrections.

According to various embodiments of the present teachings, the calibration or adjustment can comprise calibrating the emission data for variations in response to individual dyes, fluorescent marker, or other reference material. This can be done by measuring the fluorescence, signal information, or other output from a nucleic acid amplification, or other reaction, analysis, or process that use the dyes, fluorescent markers, or other reference materials. Each sample well, container, or other support region, can be prepared to contain a single dye, fluorescent marker, or other reference material that can change throughout an amplification reaction, analysis, or other process. Each sample well, container, or other support region can be prepared to contain a plurality of dyes, fluorescent marker, other reference material, or any combination thereof that can exhibit a detectable property that can change during an amplification reaction, analysis, or other process.

According to various embodiments, assays can be detected by an optical detection system having a set of filters, lenses, channels, or a combination thereof, which can be adapted to detect an emission wavelength of the one or more dyes, fluorescent marker, or other reference material. The dye or dyes or other materials can comprise dyes such as VIC, FAM, TAMRA, NED, JOE, ROX, or other dyes or combinations of dyes or materials. The change in a detected signal or detected signals can be derived using the filters, lenses, channels, or a combination thereof, to determine a spectral calibration matrix for a respective dye in a respective well. Techniques for generating a spectral calibration matrix are described, for example, in U.S. Pat. No. 6,991,712 B2 to Sharaf et al., and in U.S. Patent Application Publication No. US 2006/0138344 A1, entitled "Spectral Calibration Method and System for Multiple Instruments" to Gunstream et al., each of which is incorporated herein by reference in its entirety.

According to various embodiments, calibrating or adjusting the spectral response to one or more dyes, fluorescent marker, or other reference material, by conducting an endpoint PCR, RT-PCR, or other reaction, process, amplification, assay, or analysis, can provide a more accurate representation of the dye signal, information signal, or other output. This method of detection can be done at an endpoint, on a real-time basis, on a cycle per cycle basis, or at any other time, point, or points in the reaction, process, amplification, assay, or analysis. According to some embodiments, by calibrating or adjusting the spectral response at each cycle of a multi-cycle process, a more precise calibration, compensation, adjustment, normalization, or other correction can be achieved.

According to various embodiments of the present teachings, the calibration or adjustment can comprise utilizing a universal reference standard or group of standards or other normalization methods that can calibrate the dye, fluorescent marker, or other reference material. A universal reference standard can be used to calibrate multiple dyes, fluorescent markers, or other information signals used in a reaction, assay, amplification, analysis, or other process, for example, the reference standard can be formulated to spectrally behave similarly to, or exactly like, one or more dye. With this reference standard or group of standards, a well plate, sample support, or other platform, or a location in a well plate, sample support, or other platform, can be calibrated for one or more dyes, fluorescent markers, or reference materials at a time.

According to various embodiments, the spectral response of the universal reference standard or standards need not match the spectral response of each of a plurality of individual dyes. If the spectral behavior of the universal reference standard does not match all subject dyes, according to various embodiments, the behavior or response of one or more dyes can be predicted or generated using a transformation, alteration, or other method, based upon the universal reference standard. The universal reference standard can comprise solid material, liquid material, one fluorescent dye or material, multiple fluorescent dyes or materials, or any combination of types of materials.

According to various embodiments of the present teachings, spectral calibration can comprise suspending, inserting, wrapping, applying, or some other method of capturing and/or encapsulating each dye, fluorescent marker, or other reference material used for spectral calibration in a medium that can comprise, for example, a solid, a polymer, or another medium. The suspension, insertion, application, or other method of capturing or encapsulating the one or more dyes or other substances in the medium, can enable a dry or solid substance to exhibit similar spectral responses compared to wet dyes, wet media, or other wet material. The use of a dry chemical or solid material can help to eliminate the drawbacks of wet chemistry, such as, evaporation, condensation, sloshing, storage stability, lifetime, expiration, and various other drawbacks.

According to various embodiments of the present teachings, the dyes, fluorescent markers, or other reference materials used to perform calibration or adjustment, can be placed, loaded, inserted, enclosed, wrapped around, or otherwise built into locations other than the sample wells or containers, for example, built into the interstitial spaces on a multi well plate, sample support, or other platform. By using the interstitial spaces, the individual wells or containers of the plate, platform, or other support can be loaded with an analyte, dye, reaction material, or some other material, for example, samples of DNA fragments, to which one or more spectrally distinct dye, fluorescent marker, or other reference material can be reacted with or attached for detection and/or analysis. At the same time, a calibration of the emission data can be established by detecting signals from the interstitial spaces that have a dye or other reference material built therein.

According to various embodiments of the present teachings, the calibration or adjustment can comprise performing a calibration on emission data from a system, apparatus, device, or other instrument, in which there are more spectral channels or filters than there are dyes. These systems or other instruments can be used to adjust an estimated calibration matrix by calculating the mean squared error (MSE) as amplification occurs. The calibration of such systems can be significantly affected by the off-axis elements of the corresponding calibration matrix. According to some embodiments, an adjustment can be made to a known, approximate, calibration matrix, in a run employing more filters than dyes.

Figure 2:
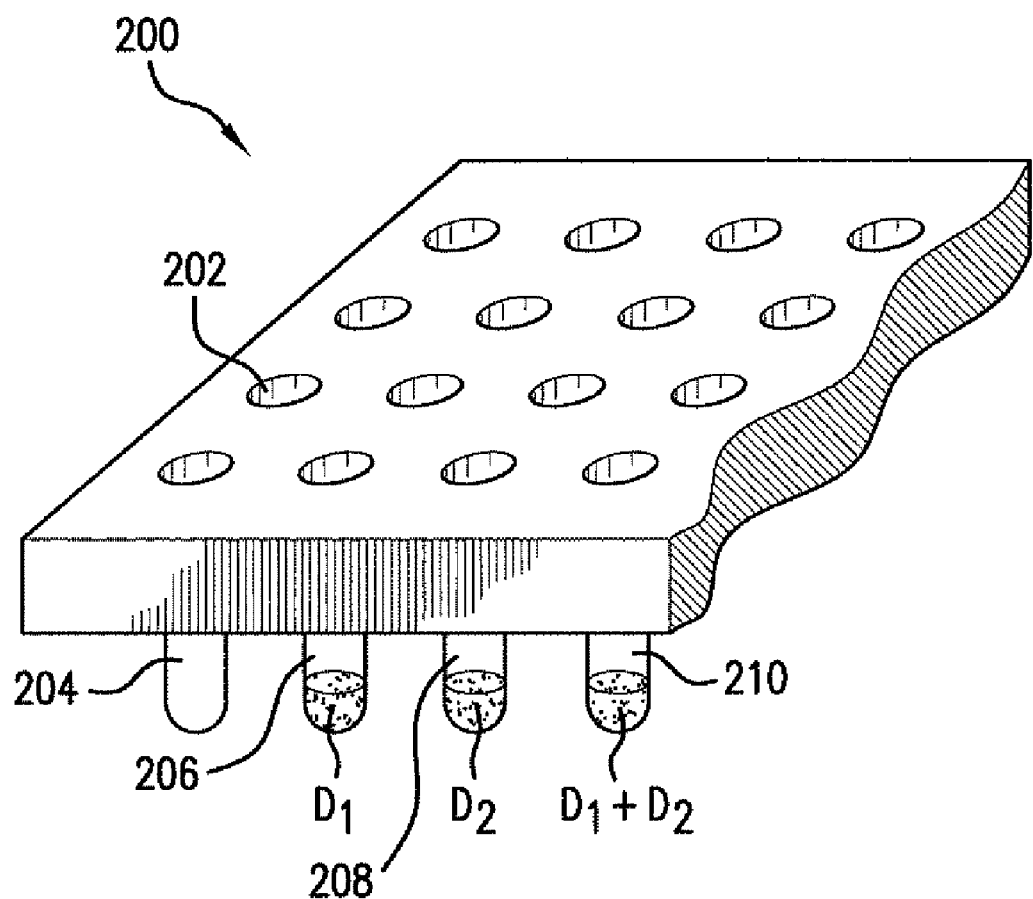
FIG. 2 illustrates a sample well plate containing sample wells, and a combination of dyes loaded into the wells, according to various embodiments.

According to various embodiments of the present teachings, the calibration or adjustment can comprise the calibration of emission data from multiple dyes, fluorescent markers, or other reference materials that are loaded in the same well plate, sample support, or other platform. The sample wells, containers, or other support regions on the well plate, sample support, or other platform, can be interspersed with reference sample wells, containers, or other support regions on the same well plate, sample support, or other platform. The reference sample wells, containers, or other support regions can be loaded with different dyes, fluorescent markers, or other reference materials. The loaded sample wells, containers, or other support regions used for calibration can therefore be spread across the well plate, sample support, or other platform, such that more than one dye, fluorescent marker, or other reference material, can be calibrated at one time. As illustrated in FIG. 2, for example, a portion of a multi-well plate 200 comprises a plurality of wells 202. The plurality of wells 202 can comprise empty wells 204, wells 206 comprising a first dye D1, wells 208 comprising a second dye D2 that differs from dye D1, and wells 210 comprising both dyes D1 and D2.

Figure 3:
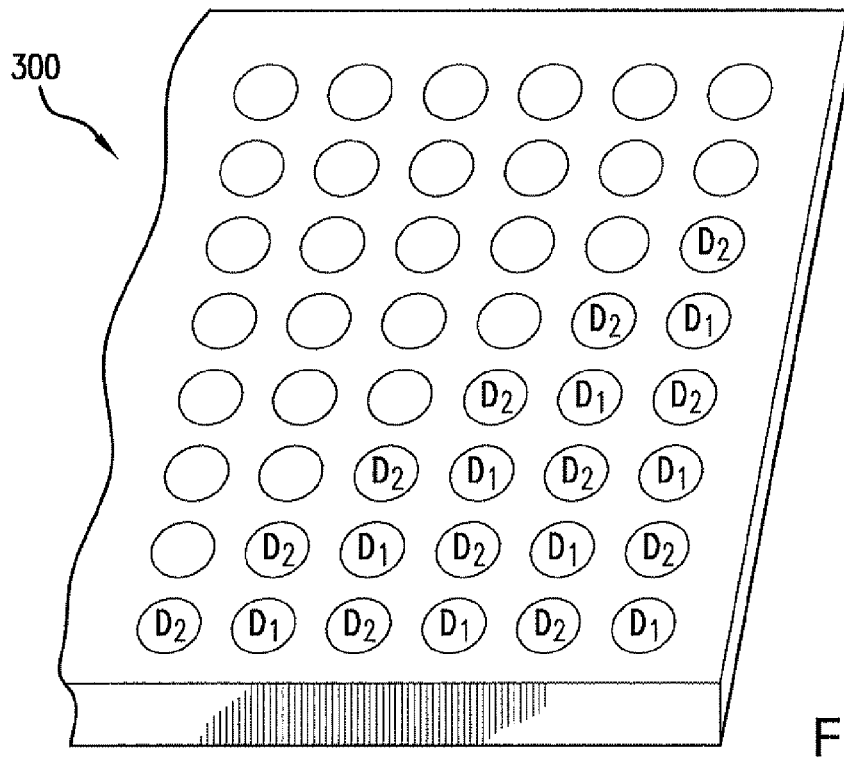
FIG. 3 illustrates a top perspective view of a portion of a sample well plate loaded with two different dyes in an alternating, horizontal pattern, according to various embodiments.
Figure 4:
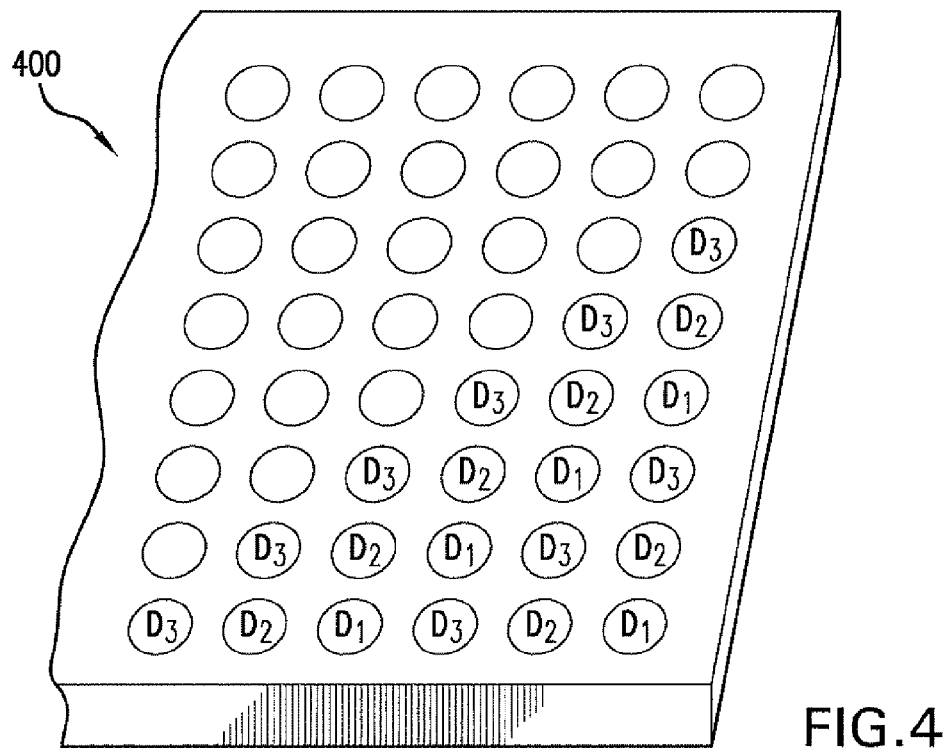
FIG. 4 illustrates a top perspective view of a portion of a sample well plate loaded with three different dyes in an alternating, horizontal pattern, according to various embodiments.

According to various embodiments, various amounts of dyes, fluorescent markers, or other reference materials can be used on the same well plate, sample support, or other platform, for example, one dye, two dyes, three dyes, or more than three dyes. In some embodiments, two or more dyes can be loaded such that each dye is inserted into sample regions in a predetermined format or pattern. For example, the pattern can comprise a diagonal or alternating format as seen in FIG. 3, where a portion of a sample well plate 300 is shown with 2 different dyes D1 and D2, alternating from one well to the next well of sample well plate 300. In another example, as shown in FIG. 4, a portion of sample well plate 400 can contain 3 different dyes D1, D2, and D3, that can be disposed in an alternating pattern for one well to the next in sample well plate 400. It will be appreciated that an alternating pattern is not the only type of predetermined pattern that can be utilized. Any predetermined pattern can be used, for example, filling each row with a particular dye, filling one half of the plate with a particular dye, filling specific areas of the plate with a specific dye, or disposing one or more dyes in any other predetermined pattern. The loaded wells can also be dispersed randomly throughout the well plate, sample support, or other platform. It will be appreciated that while dyes, fluorescent markers, or other reference materials can be loaded or disposed randomly throughout the well plate, sample support, or other platform, they can also be filled to random levels or predetermined levels, in each sample well, container, or other support region.

Figure 5:
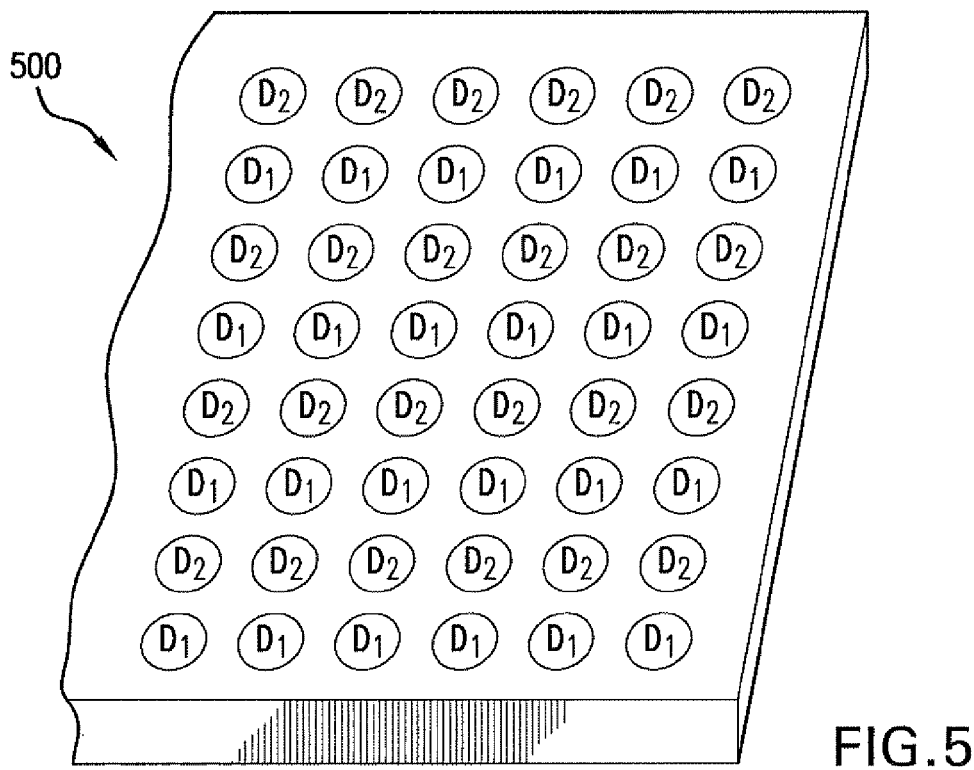
FIG. 5 illustrates a top perspective view of a portion of a sample well plate loaded with two different dyes in a different alternating pattern, according to various embodiments.

According to various embodiments, a plurality of different dyes can be used and each dye can be disposed in one or more support regions. Each dye can independently be disposed in the same number of support regions, or a different number of support regions, relative to the number of support regions that at least one other dye is disposed in. In some embodiments, each of a plurality of different dyes can be disposed in the same number of support regions relative to the number of support regions in which each of the other dyes is disposed. In some embodiments, a dye which provides a constant signal across a multi-region platform can be disposed in relatively few regions of the platform whereas dyes that vary more in detected signal intensity can be disposed in relatively many regions of the platform. For example, as illustrated in FIG. 5, a portion of a sample well plate 500 shows a first dye D1 and a second dye D2, wherein first dye D1 is loaded into a first row of wells, second dye D2 is loaded into a second row of wells, and the pattern repeats itself. Using an entire row for one dye, and the next row for a different dye, and repeating the pattern, can create an equal number of loaded wells for both dye D1 and dye D2. For example, on a 96 well microtiter plate, dye D1 would be loaded into 48 wells and dye D2 would also be loaded into 48 wells. This is just one example and is not meant to limit the different combinations that can be used. In a second example, first dye D1 can be loaded into 32 wells of a standard 96 well microtiter plate, second dye D2 can be loaded into 32 different wells of the sample plate, exclusive of dye D1, and a third dye D3 can be loaded into the remaining 32 wells, exclusive of both dye D1 and dye D2. Different combinations and different numbers of different dyes or other reference materials can be included on a single well plate, sample support, or other platform.

According to various embodiments, and as shown in these illustrations, only one dye is placed in a particular sample well, container, or other support region during the calibration process, however, multiple dyes can be placed into the individual wells or containers, during an assay, amplification reaction, or other reaction. It will be appreciated that there is no limit on the possible patterns and placements of various dyes, or other reference materials, throughout the well plate, sample support, or other platform. Different types of materials, and different variations on patterns and placements can be used. Different numbers of dyes, fluorescent markers, or other reference materials can be used, and more than one dye can be loaded into each individual well, container, or support region.

Figure 6:
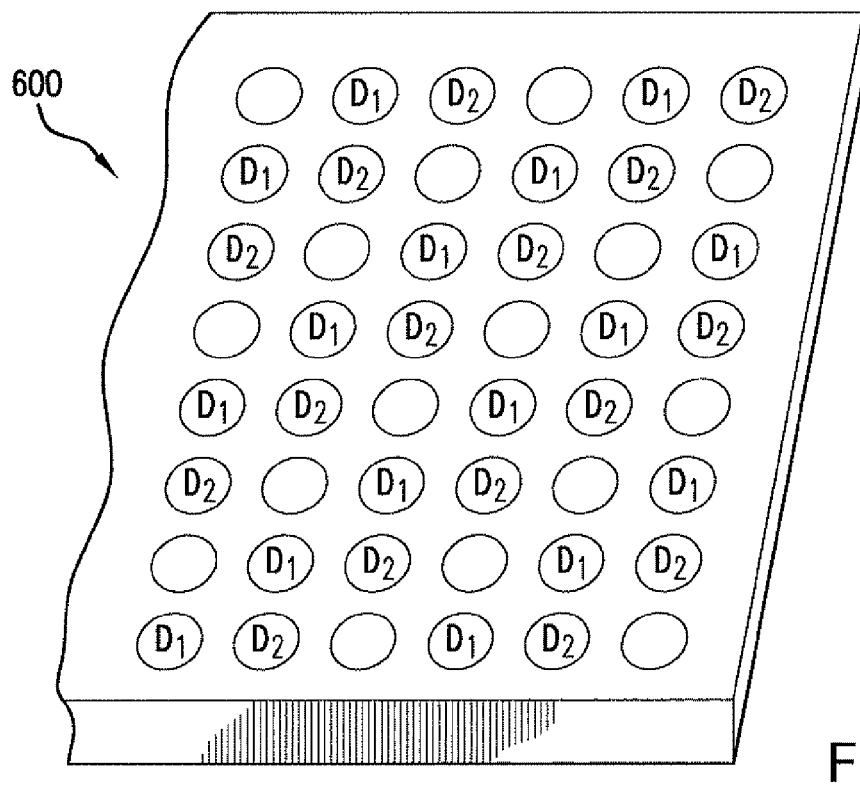
FIG. 6 illustrates a top perspective view of a portion of a sample well plate loaded with two different dyes, and also wells left empty, in an alternating, horizontal pattern, according to various embodiments.

According to various embodiments, the wells, containers, or support regions that are loaded with one or more dyes, fluorescent markers, or other reference materials, can be interspersed on the same well plate, sample support, or other platform, with wells that are loaded with a different dye or dyes, and/or they can be interspersed with empty sample wells, containers, or other support regions. In some embodiments, the loaded wells and empty wells used for calibration can be spread across the well plate, sample support, or other platform, in a predetermined format or pattern. Another example is illustrated in FIG. 6, wherein a portion of a sample well plate 600 is shown, and wells with a first dye D1, wells with a second dye D2, and empty wells are arranged in an alternating horizontal pattern. The predetermined format is not limited to this type of pattern or to using two dyes, and it will be appreciated from some embodiments, that different numbers of dyes can be used, different predetermined patterns can be used, and multiple patterns can be used at the same time on the same platform.

According to some embodiments, the loaded wells and empty wells used for calibration can be dispersed randomly across the well plate, sample support, or other platform. For example, each dye, fluorescent marker, or other reference material can be loaded into a different number of wells, containers, or support regions. For example, 40 wells can be loaded with a first dye D1, 30 different wells can be loaded with a second dye D2, and 26 different wells can be left empty. The empty wells, the wells containing dye D1, and the wells containing dye D2, can be randomly arranged.

According to some embodiments, the well plate, sample support, or other platform, can be left empty. By leaving the well plate empty, the machine, system, apparatus, device, or other instrument to be calibrated, can be calibrated to adjust for unwanted signals coming from the empty well plate, sample support, or other platform. The unwanted signals, which can occur from the well plate, sample support, or other platform, can include, but are not limited to, spurious signal contributions such as the residual fluorescence contributed by the plastic or other material of the platform, the fluorescence of a running buffer or other non-reactant liquid material, the thickness, temperature, design, or other property of the platform, and other causes of unwanted signals. With the combination of separate dyes, fluorescent markers, or other reference materials, and empty sample wells, containers, or other support regions, two or more calibrations and/or adjustments can be performed at the same time. A calibration and/or adjustment of the emission data can be performed for the unwanted signals from one or more dyes, fluorescent markers, or other reference materials, and at the same time, a calibration and/or adjustment of the emission data can be performed for unwanted signals such as signals from the plastic or other material of which the well plate, support container, or other platform can be made.

According to various embodiments, the system can use a method of interpolation, spatial interpolation, or another calculation method that takes known data values to determine, estimate, generate, or approximate unknown data values. The system and methods described herein can generate, determine, estimate, or approximate the well calibration and/or adjustment value for emission data for those sample wells, containers, or other support regions in a well plate, sample support, or other platform that are left empty, or that contain one or more dyes or other reference materials. In some embodiments, biological scanning systems detect the fluorescence output or other signal information from a sample well, container, or other support region, and then travel to a next location to detect output at that next location. In some embodiments, the system does not have to step or repeat across an entire platform. Detection does not need to be taken from each individual support region. A value for the regions that did not have a reading taken, can be estimated, approximated, or otherwise determined from the readings that were taken by the detector. According to some embodiments, data values detected, read, or imaged from the detection unit, which are faulty or in error, can be excluded from the interpolation process by comparing the data values detected, read, or imaged to a predetermined range of values. The predetermined range of values can be a range that is considered to encompass appropriate values. Using this comparison, values found not to be in the predetermined range, or outliers, can be thrown out or removed, thus creating a more efficient calculation, approximation, estimation, or other determination.

According to some embodiments, the method of interpolation, spatial interpolation, or other calculation can include, but is not limited to, detecting or receiving an emission value for a given dye, fluorescent marker, or other reference material throughout a specific row or column of wells, containers, or other regions of the sample support, while skipping over empty regions and/or regions that contain a different reference material. The detected values can be used to determine or approximate the emission data value for the empty regions and/or regions that contain different reference material, in that same row. Another method of interpolation can include, but is not limited to, detecting or receiving an emission data value for a given dye, fluorescent marker, or other reference material, throughout an entire sample support, while skipping over the wells, containers, or other regions that contain a different dye, or regions that are left empty. The detected emission data values can be used to determine or approximate the emission data value for one or more of those support regions that were skipped. In another example, the interpolation can comprise, but is not necessarily limited to, taking an average of more than two adjacent sample regions, on a sample support, which contain a given dye, and using that to determine, generate, or approximate the emission data value for an empty region, or a region that contains a different dye. The adjacent sample wells, containers, or other support regions can be located in predetermined locations throughout the well plate, support, or other platform, or at random locations throughout the well plate, support, or platform. According to various embodiments, it will be appreciated that a variety of interpolation processes, functions, or calculations adapted to determine unknown values from known values, can be used to determine, generate, or approximate emission data values for unknown signal information from wells, containers, or other support regions.

Figure 7:
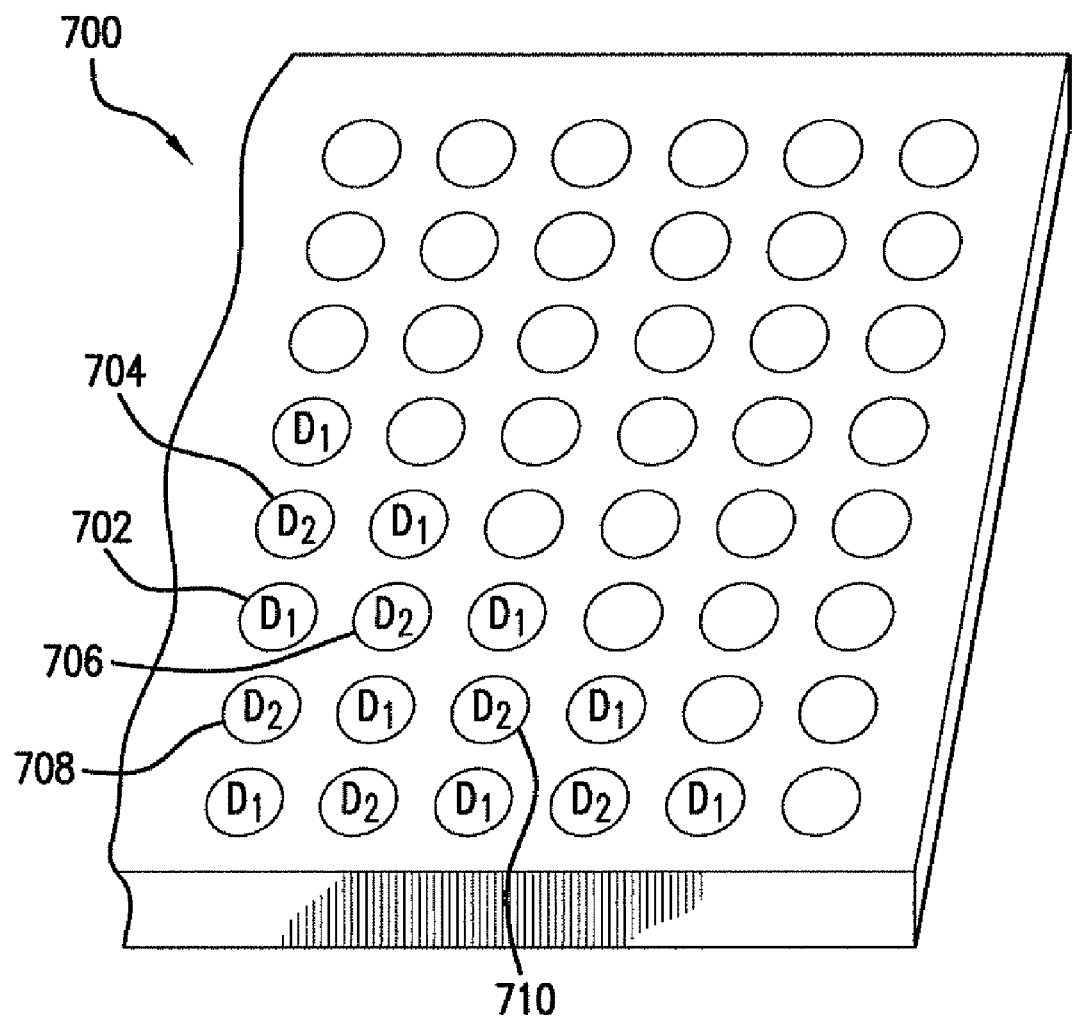
FIG. 7 illustrates a top perspective view of a portion of a sample well plate loaded with two different dyes in an alternating pattern, according to various embodiments.

According to various embodiments, and as shown in FIG. 7, for example, the interpolation can comprise different calculations, estimations, approximations, or determinations, and the interpolation can be achieved using a different number of wells at different locations on a multiwell plate 700. A portion, for example, multiple wells of multiwell plate 700, can be loaded with a first dye D1 and with a second dye D2. The two dyes can be disposed or loaded throughout the portion of the multi well plate 700, for example, as illustrated, where the dyes are disposed in an alternating format. According to various embodiment, while individual well 702 contains dye D1, an emission data value for D2 can be interpolated for individual well 702, for example, using the emission data readings received from individual wells 704, 706, and 708. In some embodiments, the average of the three can be calculated, and that average value can be used as the approximation or estimation for the emission data reading for individual well 702. It will be appreciated that this is not the only method for interpolating a value for individual well 702. The interpolation can instead result from averaging emission data values from different wells, for example, from wells 704 and 710, from wells 704 and 708, from wells 704 and 706, from wells 708 and 710, or from a combination thereof.

According to some embodiments, the method of interpolation can comprise using an algorithm instead of an average. Using the emission data detected from different wells, the values can be inserted into an algorithm, which can be used to calculate, approximate, estimate, or otherwise determine a value for an empty location or for a location containing a different dye, fluorescent marker, or other reference material. In some embodiments, given two detected data emission values, a first detected data value V1, and a second detected data value V2, a third data value can be calculated, for example, using a linear interpolation algorithm. Linear interpolation can be used to estimate, approximate, or determine a third emission data value V3, from a location that is somewhere on a line between the locations analyzed that resulted in emission data values V1 and V2, or approximately on that line. According to various embodiments, the following algorithm for linear interpolation can be used:

$$V1 = (V2-V1)(V3)/(V3-V1)$$

wherein the values for V1 and V2 are known, leaving only V3 as an unknown. Therefore the algorithm can be solved to estimate, approximate, or otherwise determine a value for V3. Many other ways can be used to interpolate, for example, averaging. The algorithm shown above is exemplary only and not to be construed as limiting the present teachings.

Figure 8:
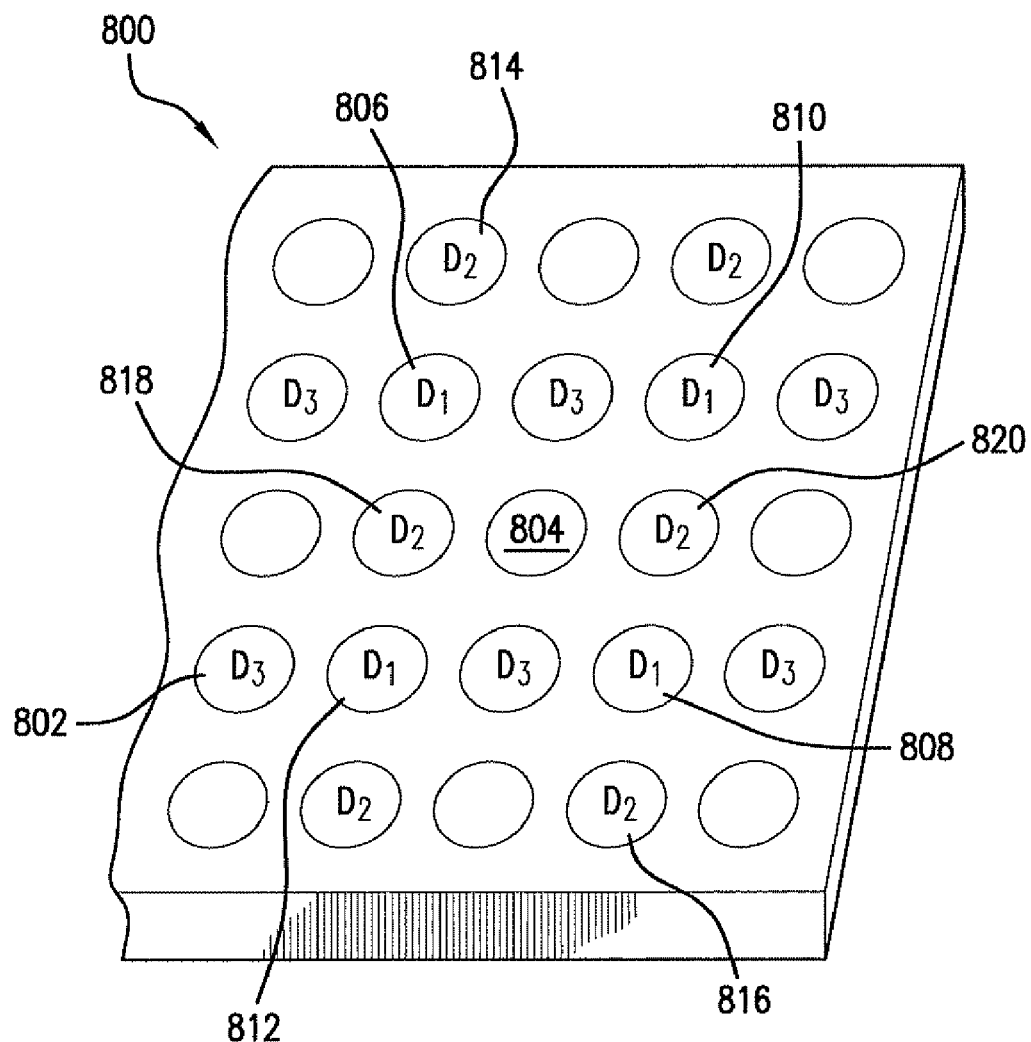
FIG. 8 illustrates a top perspective view of a portion of a sample well plate loaded with 3 different dyes in a predetermined pattern, according to various embodiments.

According to various embodiments, a method of interpolation can be used to estimate, approximate, or otherwise determine emission data values when more than one dye, fluorescent marker, or other reference material is used, and/or when some locations are left empty. As illustrated in FIG. 8, a portion of a sample well plate 800 is shown, with wells 802 loaded with 3 separate dyes, namely, a first dye D1, a second dye D2, and a third dye D3. Also, as shown in FIG. 8, some of the wells are left empty. Using interpolation, an emission data value for each of dye D1, dye D2, and dye D3, can all be estimated, approximated, or otherwise determined for any of the wells throughout the portion of the sample well plate. As shown, well 804 is located in the middle of the portion of sample well plate 800, however, this is not meant to limit the different wells, containers, or other support regions, that can have emission data estimated, approximated, or otherwise determined using interpolation. A value for emission data emitted from well 804 can be estimated, approximated, or otherwise determined for dye D1 using a method of interpolation that takes an average of the detected emission values for two adjacent wells, for example, an average of the detected emission values from wells 806 and 808, from wells 810 and 812, from wells 806 and 810, from wells 808 and 810, from wells 808 and 812, from wells 806 and 812, or from another combination of two wells.

In some embodiments, the interpolation can be performed by taking an average of the detected emission values from three wells, for example, from wells 806, 808, and 810, from wells 808, 810, and 812, from wells 806, 810, and 812, from wells 808, 810, and 812, or from any other combination of three wells. The interpolation can also be performed by taking an average of the detected emission values for more than three wells that contain dye D1, for example, from wells 806, 808, 810, and 812, or from any other number of wells that are available.

According to some embodiments, a value for emission data at well 804 can be estimated, approximated, or otherwise determined for dye D2 using a method of interpolation, for example, a linear interpolation algorithm as mentioned above. The method can interpolate using wells 814 and 816, wells 818 and 820, or any other combination of wells that that create a path between the two wells, which cuts across well 804, or such that well 804 is directly between the two wells from which actual emission data is taken. According to various embodiments, averaging and algorithms are just illustrative possibilities and are not meant to limit the various methods to approximate, estimate, or otherwise determine a value for unknown emission data. Other methods that can be used comprise, for example, spatial interpolation or three dimensional interpolation. Any of these methods, or any combination of these methods, can be used to estimate, approximate, or otherwise determine an emission data value at well 804, for dye D3, or for any other dye, fluorescent marker, or other reference material, loaded into a well plate, sample support, or other platform.

Figure 9:
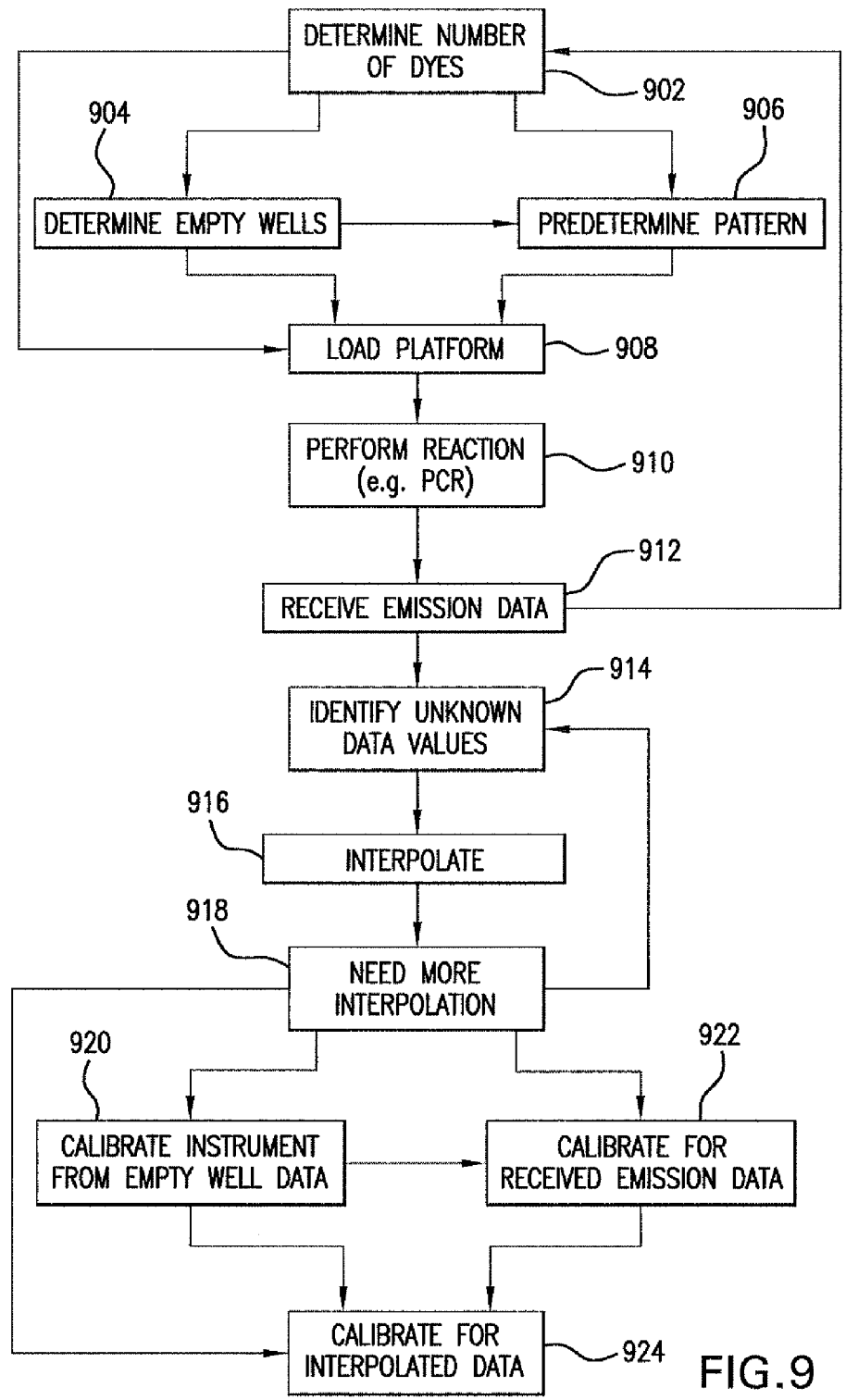
FIG. 9 illustrates a flow chart for interpolating emission data from a sample well plate, using an apparatus or instrument, such as a PCR instrument.

According to various embodiments, the interpolation process can comprise, for example, the various steps depicted in the flow illustrated in FIG. 9. The process begins with step 902, determining the number dyes that will be used in the process, reaction, amplification, or other run, for example, one, two, three, or more, different dyes. From this stage, the process can comprise selecting from three options, the first of which is step 908, loading a platform, or at least loading a portion of the platform. If empty wells are to be utilized, the process can comprise a step 904, determining the number of empty wells, and that step would come before step 908, loading the platform. If a predetermined pattern is to be utilized, the process can comprise a step 906, determining a pattern, and step 906 should also come before step 908, loading the platform. Step 906, determining a pattern, should come after step 904, determining the number of empty wells. After the platform has been loaded, the process, reaction, amplification, or other run can be performed in step 910. Step 910 can comprise, for example, a PCR or an RT-PCR run. The emission data or information signal created by the reaction or other analyses, from the dye, fluorescent marker, or other reference material, can be read by a photodetector, or other detector, and the information can be received in a step 912.

In some embodiments, the method can comprise storing the data and continuing on with more processes, reactions, amplifications, or other runs, and beginning the process all over again at step 902, determining the number of dyes. Alternatively, the process can use the emission data collected and begin a calibration process. To begin a calibration process, a determination of unknown data values 914 can be used to enable the system to determine which wells, containers, or other support regions have emitted data, and which do not. For those wells, containers, or other regions that have no emitted data for a certain dye, an interpolation 916 can be performed, using the received emission data for that dye. The unknown data values for a dye can then be estimated, determined, or approximated. The method of interpolation can involve taking an average of the known data, putting the known data into an algorithm, or some other method of calculating unknown data from known data values.

According to various embodiments, each different dye loaded into the well plate, sample support, or other platform can have an interpolation process run for it. The process can be programmed to carry out a step 918, determining whether there needs to be more interpolation. If so, the process can begin with identifying unknown data values for a certain dye 914. If no more interpolation is needed, a calibration process can then occur. The calibration process can occur at step 924, using only the interpolated data, using only the received emission data 922, or using only the well plate data obtained from empty wells in step 920. The calibration process can also comprise using all three types of data, calibrating for the interpolated data in step 924, calibrating for received emission data in step 922, and calibrating the empty well data in step 920. In some embodiments, the calibration process can comprise a combination of two of these three steps, for example, calibrating for the interpolated data in step 924, and calibrating for the empty well data in step 920, or any other combination of these steps 920, 922, and 924.

According to various embodiments, the well plate, sample support, or other platform can contain dyes, fluorescent markers, or other reference materials, used to perform calibration, preloaded, into locations other than the sample wells or containers, themselves. These other locations can comprise locations contained in or on a well plate, sample support, or other platform and the locations comprise a wet dye, a dry dye, a solid dye, different dyes, multiple dyes, any combination thereof, or left empty.

According to some embodiments, using interpolation and interstitial spacing together during a process, reaction, amplification, or other run, for example, during a PCR run or during an RT-PCR run, can enable a calibration to occur using the dyes, fluorescent markers, or other reference materials contained inside the sample wells or containers. At the same time, a calibration can occur using the dyes, fluorescent markers, or other reference materials interstitially spaced throughout the well plate, sample support, or other platform. The incorporation of both techniques can conserve both time and expense, because calibration can be performed for the dye, fluorescent markers, or other reference materials in the wells or containers, and a calibration can be performed for the dye, fluorescent marker, or other reference material interstitially spaced throughout the well plate, sample support, or other platform.

According to various embodiments, the calibration operations and related systems and methods can be further used to produce various uniformity corrections, calculations, or adjustments. Emission data detected and processed according to embodiments described herein can be used to generate a uniformity comparison or correction on a plate-to-plate basis, on a filter-to-filter basis, on an instrument-to-instrument basis, or on another basis. In some embodiments, for example, a uniformity correction can be generated to ensure that emission data detected for the same dye will produce a uniform range of outputs when that dye is loaded into any of a set of different sample plates. According to various embodiments, a plurality of sample plates or other supports or platforms can be processed to derive individual emission data from each plate or other support, using the same dye or set of dyes, or other reference materials. The intensity readings, spectral readings, and other detected emission data from those plates or other supports can be detected and recorded so that they can be compared to each other. For example, according to various embodiments, the intensity ranges or spectral response based on a first dye or set of dyes can be detected and recorded for all plates in a set of plates.

The range of absolute detected signal intensity can vary across individual plates within that group of plates, for instance, due to differences in background fluorescent emissions, manufacturing tolerances, transparency, or other characteristics of the plates or other supports. According to various embodiments, a correction factor can be generated for each subject dye for each plate, so that, for instance, the absolute value of the intensity can be scaled by a factor specific to each plate to ensure that dye readings for each given dye will be consistent, when compared across various plates. In some embodiments, the uniformity correction or adjustment can be repeated for multiple dyes across each of the plates or other supports being analyzed. In some embodiments, the uniformity correction can be generated by taking reference readings for more than one dye or other reference material in each plate, at one time.

According to various embodiments, a sample plate or other support having a known or calibrated spectral response can be used to generate a uniformity correction for the spectral filters and channels for a set of instruments. A sample plate, or a set of plates whose spectral characteristics have been corrected for uniformity, can be inserted into an instrument to generate readings of the spectral response for one or more filters present in the instrument. The filter output can be adjusted or corrected to a known uniform standard or scale. A sample plate, or a set of plates whose intensity characteristics have been corrected for uniformity, can be inserted into an instrument to generate readings of the intensity or output level for that instrument. For example, the intensity range can be corrected to a uniform scale of 0 to 1, or other limits or ranges.

According to various embodiments, the output intensity of an instrument can be expressed in relative intensity units (RIUs), or other scales, dimensions, or units. According to various embodiments, the spectral and intensity output of each instrument can be corrected or adjusted by a uniformity correction, to ensure that the spectrum and/or output levels produced by each instrument conforms to a consistent scale or range. The correction or adjustment of the output characteristics of multiple instruments can permit the direct comparison of detected emission data collected by those instruments, on a uniform basis or scale.

According to various embodiments, the set of uniformity corrections or adjustments can be carried out on a set of plates or other supports, instruments, or other components, hardware, or equipment, at the time of manufacture. The uniformity correction, scaling, calibration, or other adjustment can be stored in electronic memory, such as in a read-only memory (ROM) embedded in an instrument, or in a database stored on a local or remote server or other resource. The uniformity correction, scaling, calibration, or other adjustment can be stored in portable media, such as on a CD-ROM or other optical or electronic memory storage device. According to some embodiments, a uniformity correction can be performed to calibrate a sample plate or other support at any time during the operational use or life cycle of that support, or to calibrate filters, instruments, or other equipment, at any time during the operational use or life cycle of that equipment.

According to various embodiments, more than one type of uniformity correction can be combined together. For example, a uniformity correction for sample plate variations can be combined with a uniformity correction for intensity or spectral response of an instrument. The uniformity correction on a per-plate basis or on a per-instrument basis can be conducted at the same time as the other uniformity correction, or at different times. The dye or other reference material used for performing uniformity correction can comprise liquid or other material loaded into sample wells of a standard sample plate. According to various embodiments, the dye or other reference material used for performing uniformity correction can comprise embedded liquid or other material embedded in, encapsulated in, or affixed to interstitial spaces, interstitial cavities, or other locations adjacent or outside wells or other regions of a support. According to various embodiments, the dye or other reference material used to perform uniformity correction can be loaded in less than all the wells or locations of the support. The emission data for the wells or locations that are not loaded with dye or other reference material can be interpolated or estimated according to methods described herein.

According to various embodiments, the calibration or adjustment of emission data, emission signals, or some other signal information, can be performed in separate planes. A well plate, when imaged or detected from above, as shown in FIG. 3, FIG. 4, FIG. 5, and FIG. 6, can appear as a two dimensional view, or in a 2 dimensional plane. The detect image has a width and a length, and it is possible to interpolate values for points in that image that are contained in that two dimensional plane. Various points in the plane can be identified with an X coordinate for the length, and a Y coordinate for the width. Using these points, an approximation for any point on the plane can be made using a method of interpolation that uses data emission detected from other points in the plane. According to some embodiments, the image can be taken and viewed in three dimensions. The extra dimension can allow for movement along a Z axis, up and down from the top of the well plate, support region, or other platform. Such a method can allow for interpolation to be performed in three dimensions, for example, for a support region that is in the shape of a cube, or block, and that has a width, X, and length, Y, and a height, Z. In some embodiments, data emission can be detected from the support region at a first point in the image and that first point can be located at coordinate X1, Y1, and Z1. Another data emission can be detected at a second point located at coordinate X2, Y2, and Z2, in the support region. In some embodiments, a method of interpolation, for example, a linear interpolation algorithm, can be used to estimate, approximate, or otherwise determine a data emission value for some point located on a path, or near a path, between the first point and the second point.

According to various embodiments, these examples are just illustrative possibilities and are not meant to limit the different algorithms, equations, and estimations that can be used, and are not meant to limit the different locations, different numbers of points, and different areas of a support region, that can be used.

According to various embodiments, the calibration can comprise normalizing a pure dye calibration to the highest filter signal, and ignoring relative intensities. According to other embodiments, the calibration can comprise correcting for non-uniformity using relative intensities.

According to various embodiments, the calibration can comprise utilizing a calibration dye, a mixture of calibration dyes, or other detectable material dispersed or dissolved within a reaction mixture in every location of a support platform, to correct for optical non-uniformity or other sources of non-uniformity. According to various embodiments, the optical uniformity correction can comprise detecting only a subset of regions of the platform, for example, wells in a plate, and utilizing interpolation across unknown regions or wells.

According to various embodiments, the calibration can involve a well plate, sample support, or other platform comprising uniformity and spectral calibration locations or wells that are dispersed throughout the plate, and multiple interpolations can be carried out to perform both spectral and uniformity calibrations on one platform.

According to various embodiments, various exemplary teachings are illustrated in the document entitled "Applied Biosystems Step One Real-Time PCR System Getting Started Guide," (Applied Biosystems, Foster City, Calif.), which is incorporated herein in its entirety by reference.

Various embodiments of the present teachings can be implemented, in whole or in part, in digital electronic circuitry, or in computer hardware, firmware, software, or combinations thereof. Apparatuses of the present teachings can be implemented in a computer program, software, code, or an algorithm embodied in machine-readable media. Such media can comprise, for example, electronic memory, CD-ROM, DVD discs, hard drives, or other storage devices or media, used for execution by a programmable processor. Various method steps can be performed by a programmable processor to generate output data by executing a program of instructions, functions, or processes on input data.

The present teachings can be implemented in one or more computer programs that are executable on a programmable system that can include at least one programmable processor coupled to receive and transmit data and instructions, to and from a data storage system or memory. The system can include at least one input device, such as, a keyboard or mouse, and at least one output device, such as, a display or printer. Each computer program, software, code, or algorithm, can be implemented in a high-level procedural or object-oriented programming language, or in assembly, machine, or other low-level language, if desired. The code or language can be a compiled, interpreted, or otherwise processed for execution.

According to various embodiments, processes, methods, techniques, and algorithms can be executed on processors that can include, for example, both general and special purpose microprocessors, such as those manufactured by Intel Corp. (Santa Clara, Calif.) or AMD Inc. (Sunnyvale, Calif.). The processors can also include digital signal processors, programmable controllers, or other processors or devices. According to various embodiments, a processor can receive instructions and data from a read-only memory and/or a random access memory. A computer implementing one or more aspects of the present teachings can, in some embodiments, comprise one or more mass storage devices for storing data files, such as magnetic disks, internal hard disks, removable disks, magneto-optical disks, CD-ROM disks, DVD disks, Blu-Ray disks, or other storage disks or media.

According to various embodiments, memory or storage devices suitable for storing, encoding, or embodying computer program instructions or software and data can comprise, for example, all forms of volatile and non-volatile memory. This type of memory can comprise, for example, semiconductor memory, random access memory, electronically programmable memory (EPROM), electronically erasable programmable memory (EEPROM), flash memory, optical memory, and magnetic memory such as memory stored on magnetic disks, internal hard disks, removable disks, and magneto-optical disks. Any of the foregoing can be supplemented by, or incorporated in, ASICs. In some embodiments, processors, workstations, personal computers, storage arrays, servers, and other computer, information, or communication resources used to implement features of the present teachings, can be networked or network-accessible.

It will be appreciated that while various embodiments described above involve the calibration of one or more aspects of instrument reading, dye selection, support preparation, or other calibrations, in various embodiments more than one type of calibration can be performed, simultaneously or in sequence.

Other embodiments will be apparent to those skilled in the art from consideration of the present specification and practice of the present teachings disclosed herein. It is intended that the present specification and examples be considered as exemplary only.

What is claimed is:

1. A method of calibrating emission data for a sample support including a plurality of support regions, comprising:
    loading a detectable material into the plurality of support regions of a sample support, such that at least a first support region, but less than all, of the plurality of support regions contain the detectable material;
    receiving emission data values for the detectable material detected from the at least first support region of the plurality of support regions;
    identifying a second-support region of the plurality of support regions, that did not emit an emission data value for the detectable material, wherein the second support region is independent from the first support region;
    interpolating, based on the received emission data values, an emission data value for the received emission data values for the second support region; and
    calibrating the emission data based at least in part on the interpolated emission data value.

2. The method of claim 1, further comprising calibrating the emission data with the received emission data.

3. The method of claim 1, further comprising calibrating the emission data with the received emission data and the interpolated emission data.

4. The method of claim 1, wherein the detectable material comprises a dry material.

5. The method of claim 1, wherein the detectable material comprises a wet material.

6. A method of calibrating emission data for a sample support including a plurality of support regions, comprising:
    loading a first detectable material into the plurality of support regions of a sample support such that at least a first support region, but less than all, of the plurality of support regions contains the first detectable material;
    loading a second detectable material into the plurality of support regions such that at least a second support region, but less than all, of the plurality of support regions contains the second detectable material;
    receiving emission data values for at least one of the first and second detectable materials detected from the first and second support regions;
    identifying at least one support region of the plurality of support regions that did not emit an emission data value for at least one of the first and second detectable materials, wherein the at least one support region is independent from the first and second support regions;
    interpolating, based on the received emission data values, an emission data value for the received emission data values for the at least one support region; and
    calibrating the emission data based at least in part on the interpolated emission data value.

7. The method of claim 6, further comprising calibrating the emission data with the received emission data.

8. The method of claim 6, further comprising calibrating the emission data with the received emission data and the interpolated emission data.

9. The method of claim 6, wherein first detectable material comprises a plurality of different detectable materials.

10. The method of claim 6, wherein each of the first and second detectable materials is equally distributed between two or more of the plurality of support regions.

11. The method of claim 6, wherein at least one of the first and second detectable materials is distributed in the plurality of support regions according to a predetermined pattern of support regions of the sample support.

12. The method of claim 11, wherein the predetermined pattern comprises an alternating pattern.

13. The method of claim 6, wherein at least one of the first and second detectable materials is randomly distributed in the plurality of support regions.

14. The method of claim 6, wherein two or more of the plurality of support regions are left empty.

15. The method of claim 14, wherein the support regions containing the first detectable material, the support regions containing the second detectable material, and the two or more empty support regions, are arranged according to a predetermined pattern on the sample support.

16. The method of claim 15, wherein the predetermined pattern comprises an alternating pattern.

17. The method of claim 14, wherein the support regions containing the first detectable material, the support regions containing the second detectable material, and the two or more empty support regions, are randomly arranged in the sample support.

18. A method of calibrating signal information for a sample support, comprising:
  loading a first detectable material into the plurality of support regions of a sample support such that a first support region, but less than all, of the plurality of support regions contains the first detectable material;
  loading at least a second detectable material into the plurality of support regions such that a second support region, but less than all, of the plurality of support regions contains the second detectable material;
  receiving signal information values for at least one of the first and second detectable materials detected from at least the first and second support regions;
  identifying at least one support region of the plurality of support regions, where signal information was not detected for at least one of the first and second detectable materials, wherein the at least one support region is independent from the at least the first and second support regions; and
  interpolating, based on the received signal information values, signal information for the received signal information values for the at least one support region; and
  calibrating the emission data based at least in part on the interpolated signal information.

* * * * *